(12) United States Patent
Yang

(10) Patent No.: US 10,668,022 B2
(45) Date of Patent: Jun. 2, 2020

(54) PROCESS FOR PREPARING HYPROMELLOSE HARD CAPSULE USING THERMOGELATION

(71) Applicant: SUHEUNG CO., LTD., Cheongju-si, Chungbuk (KR)

(72) Inventor: Joo-Hwan Yang, Seongnam-si (KR)

(73) Assignee: SUHEUNG CO., LTD., Cheongju-si (KR)

( * ) Notice: Subject to any disclaimer, the term of this patent is extended or adjusted under 35 U.S.C. 154(b) by 4 days.

(21) Appl. No.: 15/941,924

(22) Filed: Mar. 30, 2018

(65) Prior Publication Data

US 2019/0224128 A1 Jul. 25, 2019

(30) Foreign Application Priority Data

Jan. 19, 2018 (KR) .................. 10-2018-0006905

(51) Int. Cl.
*A61J 3/07* (2006.01)
*A61K 9/48* (2006.01)
*A61K 31/167* (2006.01)

(52) U.S. Cl.
CPC .......... *A61K 9/4816* (2013.01); *A61K 9/4833* (2013.01); *A61K 9/4883* (2013.01); *A61K 31/167* (2013.01)

(58) Field of Classification Search
None
See application file for complete search history.

(56) References Cited

U.S. PATENT DOCUMENTS 6,410,050 B1   6/2002   Yang

FOREIGN PATENT DOCUMENTS

WO   WO-03011257 A1 * 2/2003 .......... A61K 9/4816
WO   2008-050209 A1   5/2008
WO   WO-2008050209 A1 * 5/2008 .............. A61J 3/077

OTHER PUBLICATIONS

Moawia Al-Tabakha, "HPMC Capsules: Current Status and Future Prospects," J. Pharm. Pharmaceut Sci. 13(3) pp. 428-442, 2010.
M. Sherry Ku et al., "Performance qualification of a new hypromellose capsule," International Journal of Pharmaceutics, 386 (2010) pp. 30-41.

* cited by examiner

*Primary Examiner* — Brian Gulledge
(74) *Attorney, Agent, or Firm* — Hunton Andrews Kurth LLP

(57) ABSTRACT

The present invention relates to a process for preparing hypromellose hard capsule using thermogelation with improved storage stability, film strength, film distribution, filling up performance and/or bioavailability of ingredient. More specifically, this invention relates to a process for preparing hypromellose hard capsule using thermogelation with improved storage stability, film strength, film distribution, filling up performance and/or bioavailability of ingredient, comprising the steps of: i) sequentially adding and solubilizing 0.1-0.5 wt part of plasticizer, 0.1-0.5 wt part of wetting agent and a small amount of a viscosity stabilizer to the 100 wt part of hypromellose aqueous dispersion containing 19-22 wt part of hypromellose; ii) adjusting the viscosity of the mixture into 800-1,300 cP; iii) dipping the mold pin into the hypromellose aqueous solution maintained at 19-21° C. after preheating the mold pin to be 100-120° C.; and iv) forming the hypromellose hard capsule.

5 Claims, 4 Drawing Sheets

FIG. 2

PROCESS FOR PREPARING HYPROMELLOSE HARD CAPSULE USING THERMOGELATION

TECHNICAL FIELD

The present invention relates to a process for preparing hypromellose hard capsule using thermogelation with improved storage stability, film strength, film distribution, filling up performance and/or bioavailability of ingredient. More specifically, this invention relates to a process for preparing hypromellose hard capsule using thermogelation with improved storage stability, film strength, film distribution, filling up performance and/or bioavailability of ingredient, comprising the steps of: i) sequentially adding and solubilizing 0.1-0.5 wt part of plasticizer, 0.1-0.5 wt part of wetting agent and a small amount of a viscosity stabilizer to the 100 wt part of hypromellose aqueous dispersion containing 19-22 wt part of hypromellose; ii) adjusting the viscosity of the mixture into 800-1,300 cP; iii) dipping the mold pin into the hypromellose aqueous solution maintained at 19-21° C. after preheating the mold pin to be 100-120° C.; and iv) forming the hypromellose hard capsule.

DESCRIPTION OF PRIOR ART

In the case of hard capsule, a hard capsule using gelatin of an animal origin has been commercialized for a long time. Recently, due to the problems of denaturation of gelatin and relatively high water content of gelatin (11-16 wt %), a gelatin hard capsule has a handicap for filling the hygroscopic and/or water sensitive preparation. Therefore, a cellulose hard capsule, especially, a hypromellose (HPMC) hard capsule can replace the gelatin hard capsule, due to its relatively low water content (3-6 wt %).

The hypromellose capsule using thermogelation can show an excellent transparency, an uniform film distribution and an improved mechanical strength. It also can have an excellent filling up performance even in the high-speed automatic filling machine.

Such a cellulose-based hard capsule has already been disclosed by the applicant's own U.S. Pat. No. 6,410,050, 'Cellulose capsule using mixed solution of pectin and glycerin and the manufacturing process thereof'. In this patent disclosure, a cellulose capsule prepared by the steps comprising: i) preparing a mixed solution of pectin and glycerin, ii) adding said mixed solution to solubilized cellulose aqueous solution, iii) adding a small amount of glacial acetic acid, calcium gluconate, sucrose fatty acid ester to said mixture, and iv) standing by adjusting viscosity and forming a capsule has been disclosed.

On the other hand, for manufacturing a hypromellose hard capsule, the thermogelation method, especially, hot dipping method to maintain the inherent physical properties of hypromellose has been introduced, instead of the manufacturing method using chemically gelling agent and/or auxiliary gelling agent.

In PCT International patent publication WO 2008/050209 A1 'Hydroxypropyl methyl cellulose hard capsules and process of manufacture', a process for manufacture of hard hydroxypropyl methyl cellulose capsules comprising a film forming material of hydroxypropyl methyl cellulose having a methoxy content of 27.0-30.0% (w/w) and a hydroxypropoxy content of 4.0-7.5% with a viscosity of 3.5-6.0 cPs at 20° C. as 2% weight solution has been disclosed. In this disclosure, the dipping pin has been preheated to be 60-90° C. and the preheated dipping pin has been dipping into the aqueous hypromellose composition at a temperature 1.0-4.0° C. below the gelling temperature of aqueous composition. Finally, a hypromellose hard capsule has been prepared after drying the film.

In the case of the hypromellose hard capsules prepared by the above-mentioned thermogelation method, the dissolution rate in vitro can be better than that of the cellulose hard capsules using a chemical gelling agent such as carrageenan. However, in terms of in vivo bioavailability of ingredient, said hypromellose hard capsule cannot show a significant increase in bioavailability compared to that of the cellulose hard capsules using a chemical gelling agent (Please refer to Moawia Al-Tabakha, J. Pharm. Pharmaceut Sci. 13(3) pp. 428-442, 2010, 'HPMC Capsules: Current Status and Future Prospects').

The reason why hypromellose hard capsule using thermogelation shows higher in vitro dissolution rate in acidic medium or in buffer containing potassium ions can be explained that a gelling agent such as carrageenan causes the interaction between carrageenan and drug compound in the presence of potassium ions used as auxiliary gelling agent, which delays the capsule opening of cellulose hard capsule. However, it has been reported that hypromellose hard capsule can show only a slight difference in bioavailability compared to that of the cellulose hard capsules using a chemical gelling agent (Please refer to M. Sherry Ku et al., International Journal of Pharmaceutics, 386 (2010) pp. 30-41, 'Performance qualification of a new hypromellose capsule').

On the other hand, the dissolution rate and disintegration of hypromellose hard capsules using thermogelation tends to be declined even in vitro over 30° C. compared to those of cellulose hard capsule using a chemical gelling agent. Therefore, when taking the hypromellose hard capsule using thermogelation, it has been required to take it with cold water at about 10° C.

In case that 0.3 wt % or more of sodium chloride has been contained in the raw material of hypromellose for hard capsules using thermogelation, the eduction of NaCl out of the hypromellose aqueous solution can result in Plating of capsule, which forms cloudy fine stains on the inner surface of the capsule shell. Further, the reason why eduction of NaCl occurs is that the water in the hypromellose aqueous solution rapidly evaporates when the preheated mold pin at high temperature of 100-120° C. is dipping into the hypromellose aqueous solution at low temperature of 19-22° C. When the stability test is carried out in accelerated condition of 40° C./75% RH for 6 months, the transparency of hard capsule may decrease according to the lapse of time. Therefore, the storage stability of hypromellose hard capsule can be lowered.

For improving storage stability, film strength, film distribution, filling up performance and/or bioavailability of ingredient, the inventor of present invention has developed a novel process for manufacturing hypromellose hard capsule using thermogelation as follows. Accordingly, the manufacturing process comprises the steps of: i) sequentially adding and solubilizing 0.1-0.5 wt part of plasticizer, 0.1-0.5 wt part of wetting agent and a small amount of a viscosity stabilizer to the 100 wt part of hypromellose aqueous dispersion containing 19-22 wt part of hypromellose; ii) adjusting the viscosity of the mixture into 800-1,300 cP; iii) dipping the mold pin into the hypromellose aqueous solution maintained at 19-21° C. after preheating the mold pin to be 100-120° C.; and iv) forming the hypromellose hard capsule.

PROBLEM TO BE SOLVED

The problem to be solved is to develop a hypromellose hard capsule using thermogelation with improved storage stability, film strength, film distribution, filling up performance and/or bioavailability of ingredient. Further, the present invention is to develop a process for preparing a hypromellose hard capsule using thermogelation with improved storage stability, film strength, film distribution, filling up performance and/or bioavailability of ingredient comprising the steps of: i) sequentially adding and solubilizing 0.1-0.5 wt part of plasticizer, 0.1-0.5 wt part of wetting agent and a small amount of a viscosity stabilizer to the 100 wt part of hypromellose aqueous dispersion containing 19-22 wt part of hypromellose; ii) adjusting the viscosity of the mixture into 800-1,300 cP; iii) dipping the mold pin into the hypromellose aqueous solution maintained at 19-21° C. after preheating the mold pin to be 100-120° C.; and iv) forming the hypromellose hard capsule.

MEANS FOR SOLVING THE PROBLEM

The object of the present invention is to provide a process for preparing a hypromellose hard capsule using thermogelation with improved storage stability, film strength, film distribution, filling up performance and/or bioavailability of ingredient comprising the steps of: i) sequentially adding and solubilizing 0.1-0.5 wt part of propylene glycol as plasticizer, 0.1-0.5 wt part of D-sorbitol as wetting agent and 0.04-0.25 wt part of colloidal silica as viscosity stabilizer into the 100 wt part of hypromellose aqueous dispersion containing 19-22 wt part of hypromellose, and dispersing them 4 hours, wherein the amount of sodium chloride in raw material of hypromellose is less than 0.3 wt %; ii) completely solubilizing the hypromellose aqueous dispersion obtained in step i) to be transparent liquid phase by standing still for 44-52 hours at 17-23° C. in the hydration tank; iii) adjusting the final viscosity of hypromellose aqueous solution into 800-1,300 cP; iv) dipping the preheated mold pin into the hypromellose aqueous solution in the dipping pan maintained at 19-21° C. under the control of temperature control device of dipping pan, after preheating the mold pin to be 100-120° C. in the deck heater of pinbar heating part; and v) forming and drying the obtained hard capsule at 50-70° C., 20-85% of relative humidity for 40-80 minutes.

Further, said deck heater in the pinbar heating part is installed for heating the mold pin to maintain the uniform film thickness in the range of 0.08-0.12 mm, and said deck heater is constructed by stacking a ceramic sliding plate and an aluminum heating plate on the mica plate heater on the urethane insulation base, which can improve film strength, film distribution and filling up performance.

Further, said pinbar pressing device is installed for minimizing the bending of pinbar occurred when the mold pin is preheated by deck heater of pinbar heating part, and the pressing pad in the pinbar pressing device is down for pressing the upper part of mold pinbar by the pressure of compression spring, which can improve film strength, film distribution and filling up performance.

Further, said temperature control device of dipping pan is installed for maintaining the temperature of hypromellose aqueous solution in the dipping pan to be 19-21° C. stably, by controlling the supply and return of chilled water, and the hypromellose aqueous solution is stirred at 20-28 rpm in the dipping pan, which can improve film strength, film distribution and filling up performance.

Further, said D-sorbitol as wetting agent is added for improving the storage stability, by preventing the Plating of capsule in the step iv) caused by the elution of NaCl out of the hypromellose aqueous solution.

The other object of the present invention is to provice a hypromellose hard capsule using thermogelation prepared by said method, wherein the bioavailability of ingredient drug increases compared to that of cellulose capsule using a chemical gelling agent by increasing at least 5% of the AUC (Area Under Curve), when the ingredient drug is administered through the hypromellose hard capsule using thermogelation.

ADVANTAGEOUS EFFECT

The outstanding advantageous effect of the present invention is to provide a hypromellose hard capsule using thermogelation with improved storage stability, film strength, film distribution, filling up performance and/or bioavailability of ingredient, prepared by the steps of comprising: i) sequentially adding and solubilizing 0.1-0.5 wt part of plasticizer, 0.1-0.5 wt part of wetting agent and a small amount of a viscosity stabilizer to the 100 wt part of hypromellose aqueous dispersion containing 19-22 wt part of hypromellose; ii) adjusting the viscosity of the mixture into 800-1,300 cP; iii) dipping the mold pin into the hypromellose aqueous solution maintained at 19-21° C. after preheating the mold pin to be 100-120° C.; and iv) forming the hypromellose hard capsule.

PREFERRED EMBODIMENT OF INVENTION

Figure 1:
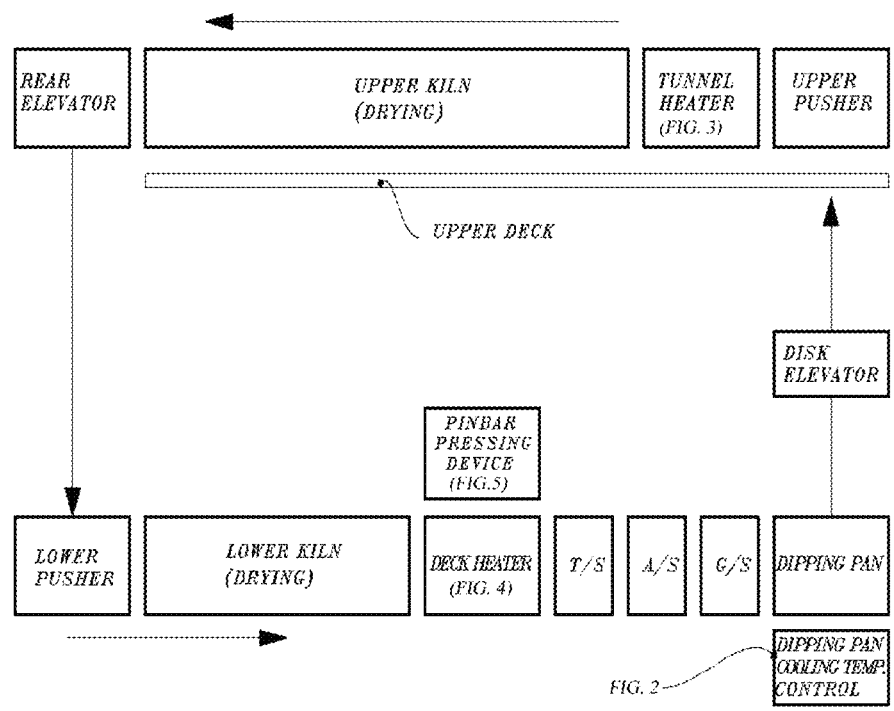
FIG. 1 is a flow chart showing a process and an apparatus for preparing hypromellose hard capsule using thermogelation of the present invention.

The present invention relates to a process for preparing a hypromellose hard capsule using thermogelation with improved storage stability, film strength, film distribution, filling up performance and/or bioavailability of ingredient comprising the steps of: i) sequentially adding and solubilizing 0.1-0.5 wt part of propylene glycol as plasticizer, 0.1-0.5 wt part of D-sorbitol as wetting agent and 0.04-0.25 wt part of colloidal silica as viscosity stabilizer into the 100 wt part of hypromellose aqueous dispersion containing 19-22 wt part of hypromellose, and dispersing them 4 hours, wherein the amount of sodium chloride in raw material of hypromellose is less than 0.3 wt %; ii) completely solubilizing the hypromellose aqueous dispersion obtained in step i) to be transparent liquid phase by standing still for 44-52 hours at 17-23° C. in the hydration tank; iii) adjusting the final viscosity of hypromellose aqueous solution into 800-1,300 cP; iv) dipping the preheated mold pin into the hypromellose aqueous solution in the dipping pan maintained at 19-21° C. under the control of temperature control device of dipping pan, after preheating the mold pin to be 100-120° C. in the deck heater of pinbar heating part; and v) forming and drying the obtained hard capsule at 50-70° C., 20-85% of relative humidity for 40-80 minutes.

Further, the present invention also relates to a hypromellose hard capsule using thermogelation prepared by said method, wherein the bioavailability of ingredient drug increases compared to that of cellulose capsule using a chemical gelling agent by increasing at least 5% of the AUC (Area Under Curve), when the ingredient drug is administered through the hypromellose hard capsule using thermogelation.

Further, such an improvement of bioavailability of hypromellose hard capsule using thermogelation of the present invention has been believed that in vivo absorption, distribution and metabolism of drug ingredient have been favorably affected by proper in vivo dissolution and disintegration performance according to the improved properties of storage stability, film strength, film distribution, filling up performance.

The present invention can be explained in detail as follows.

The hypromellose hard capsule using thermogelation of the present invention has following advantageous properties, that are, a convenience for water-sensitive hygroscopic preparation due to its relatively low water content less than 7%, an excellent transparency, a good dissolution rate, an uniform film distribution, an improved mechanical film strength, and/or an excellent filling up performance even in high speed automatic filling machine.

However, due to the presence of NaCl in the raw material of hypromellose, a plating phenomenon can occur in the hypromellose hard capsule using thermogelation, when NaCl in aqueous hypromellose solution is educed outside, which causes the decline of storage stability.

Further, the addition of D-sorbitol as wetting agent into the hypromellose aqueous solution has been introduced for preventing the plating phenomenon as well as improving the storage stability.

Therefore, the present invention has designed the optimal composition and process for preparing a hypromellose hard capsule using thermogelation, which improves the storage stability by preventing the plating phenomenon as well as the bioavailability of ingredient.

Further, the present invention has also provided a hypromellose hard capsule using thermogelation with improved storage stability, film strength, film distribution, filling up performance and/or bioavailability of ingredient, using the hypromellose aqueous dispersion sequentially adding and solubilizing propylene glycol as plasticizer, D-sorbitol as wetting agent and colloidal silica as viscosity stabilizer to the hypromellose containing less than 0.3 wt % of NaCl.

The hypromellose hard capsule using thermogelation of present invention has been prepared according to hot dipping method, in which the temperature of mold pin has been maintained over gelling temperature of hypromellose aqueous solution and the heated mold pin is dipping to the cooled hypromellose aqueous solution for gelling the capsule. Contrarily, the cellulose hard capsule using a chemical gelling agent has to be prepared according to cold dipping method.

For preparing a hypromellose hard capsule using thermogelation by hot dipping method of the present invention, the preparation method has to include following steps. The hypromellose aqueous dispersion has to be completely solubilized in a hydration tank at the temperature of 17-23° C. for 44-52 hours to be a transparent liquid phase. Thereafter, the final viscosity of the aqueous hypromellose solution has been adjusted to 800-1,300 cP, and the mold pin has been pre-heated to be 100-120° C. in the deck heater of pinbar heating part. Then, the preheated mold pin has been dipped into the hypromellose aqueous solution maintained at 19-21° C. in the dipping pan. Finally, hypromellose hard capsule has been obtained after forming and drying it at 50-70° C., 20-85% of relative humidity for 40-80 minutes.

Further, the composition of hypromellose aqueous solution for preparing a hypromellose hard capsule using thermogelation of the present invention can be explained in detail as follows.

The hypromellose as the raw material of the present invention is hypromellose having less than 0.3 wt % of NaCl, 26-31 wt % of methoxy content and 4-8 wt % of hydroxypropoxy content. Further, the viscosity is 4-6 cPs as 2 wt % of hypromellose aqueous solution at 20° C.

In order to improve the film strength and to reduce the film thickness deviation of hypromellose hard capsule, it is required to add a plasticizer, preferably, propylene glycol (PG). According to the addition of propylene glycol, when the film is pulled out, length defects, thickness defects, cracks and dents of the film can be solved. The amount of propylene glycol is 0.1-0.5 wt part as to the 100 wt part of the hypromellose aqueous solution.

The hypromellose hard capsule using thermogelation of present invention can include D-sorbitol as wetting agent. The amount of D-sorbitol is 0.1-0.5 wt part, preferably 0.2-0.4 wt part as to the 100 wt part of the hypromellose aqueous solution.

Further, the addition of D-sorbitol as wetting agent into the hypromellose aqueous solution can prevent the plating phenomenon, which can result in the improvement of storage stability.

Further, hypromellose hard capsule using thermogelation can include 0.04-0.25 wt part of colloidal silica as viscosity stabilizer. The addition of colloidal silica can control and maintain the final viscosity of hypromellose aqueous solution to be 800-1,300 cP stably.

Further, said colloidal silica has been prepared by ion exchange or acid grafting using sodium silicate or water glass as raw material. Fumed silica is preferred. It is also a stable spherical particle having 99.0-100.5 wt % of $SiO_2$ content, and pH 3.5-5.5 in the 4% aqueous solution.

A process for preparing hypromellose hard capsule using thermogelation of the present invention can be explained in detail with accompanying drawings.

FIG. 1 is a flow chart showing a process and an apparatus for preparing hypromellose hard capsule using thermogelation of the present invention.

As shown in FIG. 1, the hypromellose hard capsule using thermogelation of the present invention has been prepared by following processes comprising the steps of: preheating the mold pin to be 100-120° C. stably in the deck heater; cooling the hypromellose aqueous solution to be 19-21° C. stably in the dipping pan; dipping the mold pin into the dipping pan; and drying the capsule in the kiln.

Figure 2:
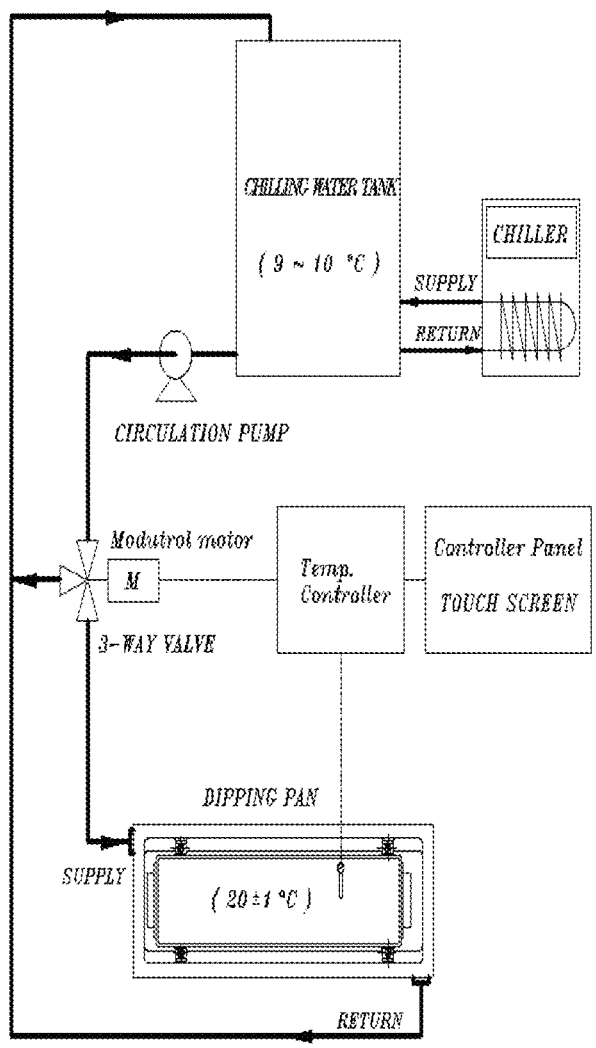
FIG. 2 is a schematic view showing the overall configuration of dipping pan cooling and temperature control device of dipping pan, which can uniformly cool and adjust the temperature of the hypromellose aqueous solution in the dipping pan in the apparatus for preparing hypromellose hard capsule using thermogelation of the present invention.

FIG. 2 is a schematic view showing the overall configuration of dipping pan cooling and temperature control device of dipping pan, which can uniformly cool and adjust the temperature of the hypromellose aqueous solution in the dipping pan in the apparatus for preparing hypromellose hard capsule using thermogelation of the present invention.

As shown in FIG. 2, for stably cooling and maintaining the temperature of hypromellose aqueous solution to be 19-21° C. in the dipping pan, following processes comprising the steps of; supplying 9-10° C. of chilling water in the chilling water tank into the dipping pan circulation pump; recovering and returning the water from dipping pan into chilling water tank; and controlling the temperature of chilling water to be 9-10° C. by temperature controller, have been required.

On the other hand, the temperature of dipping pan is stably maintained by stirring the hypromellose aqueous solution at 20-28 rpm in the dipping pan; and circulating the chilling water between dipping pan and chilling water tank using 3-way valve and modutrol motor. Further, all systems have been controlled by temperature controller.

Figure 3:
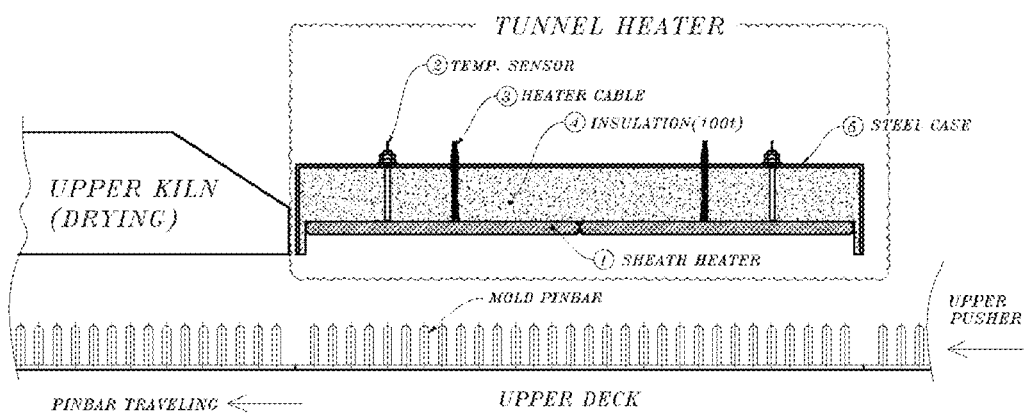
FIG. 3 is a schematic view showing the configuration of tunnel heater for controlling the flow of film in the apparatus for preparing hypromellose hard capsule using thermogelation of the present invention.

FIG. 3 is a schematic view showing the configuration of tunnel heater for controlling the flow of film in the apparatus for preparing hypromellose hard capsule using thermogelation of the present invention.

As shown in FIG. 3, in the tunnel heater, a sheath heater is equipped on its bottom and a steel case housing is surrounding the outside. Further, an insulating layer is inserted between sheath heater and steel case housing. Further, a temperature sensor is attached on the steel case housing and the heater cable is protruding.

Figure 4:
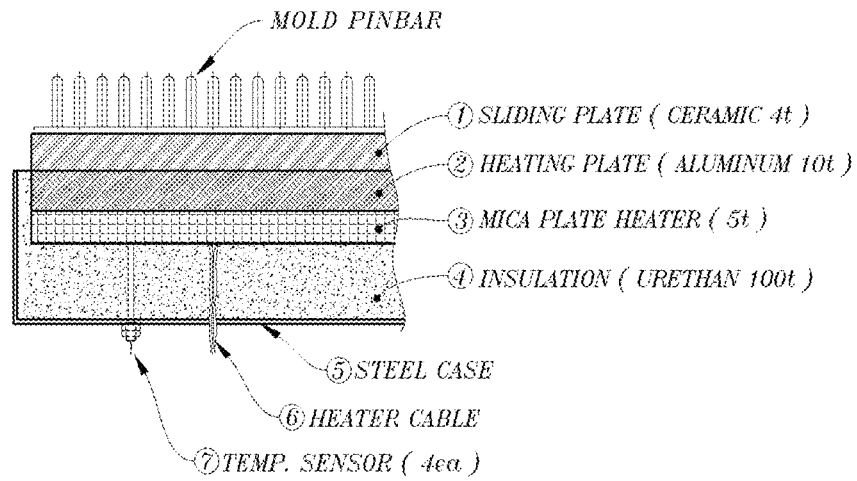
FIG. 4 is a schematic view showing the configuration of deck heater for maintaining the heating temperature of mold pin stably in the apparatus for preparing hypromellose hard capsule using thermogelation of the present invention.

FIG. 4 is a schematic view showing the configuration of deck heater for maintaining the heating temperature of mold pin stably in the apparatus for preparing hypromellose hard capsule using thermogelation of the present invention.

As shown in FIG. 4, the deck heater is equipped for heating the mold pin to uniformly form the film thickness of hypromellose hard capsule in the range of 0.08-0.12 mm. The deck heater has been prepared by sequentially stacking an urethane insulation on the bottom, a mica plate heater, an aluminum heating plate and a ceramic sliding plate to the top. Further, a steel case housing is surrounding the outside. Further, a temperature sensor is attached on the steel case housing and the heater cable is protruding.

Figure 5:
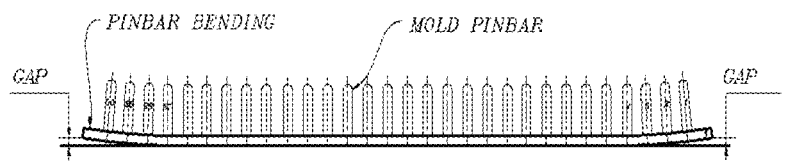
FIG. 5 is a schematic view showing the configuration of pinbar pressing device for minimizing a temperature deviation due to the bending of the mold pinbar in the apparatus for preparing hypromellose hard capsule using thermogelation of the present invention.
Figure 5:
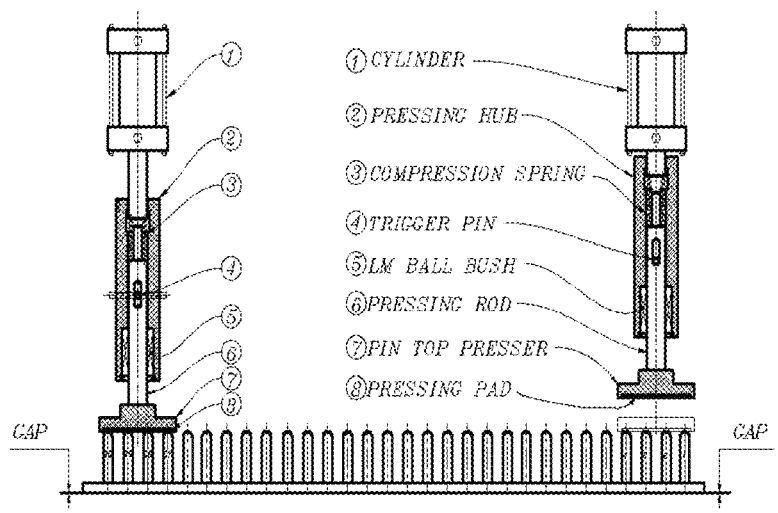

FIG. 5 is a schematic view showing the configuration of pinbar pressing device for minimizing a temperature deviation due to the bending of the mold pinbar in the apparatus for preparing hypromellose hard capsule using thermogelation of the present invention.

As shown in FIG. 5, the pinbar pressing device is equipped for minimizing the bending of pinbar occurred when the mold pin is preheated by deck heater of pinbar heating part. Further, the head parts of mold pinbars laid on the both ends of pinbar are pressed by pinbar pressing device. Further, the pressing pad in the pinbar pressing device is down for pressing the upper part of mold pinbar by the pressure of compression spring.

Figure 6:
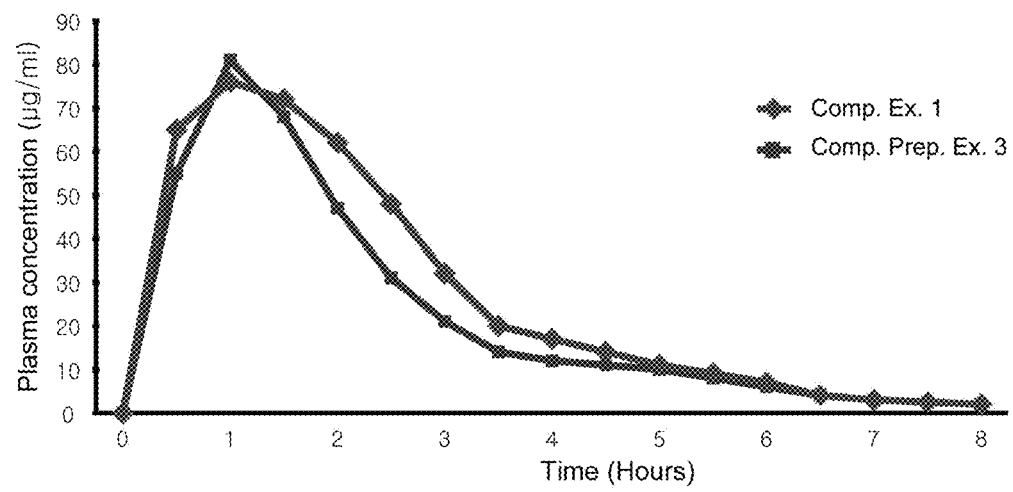
FIG. 6 is a graph showing the changes of plasma concentrations of acetaminophen according to the lapse of time, when the acetaminophen is filled and administered to the Beagles in both hypromellose hard capsule using thermogelation of the present invention and the hard capsule prepared in Comparative Preparation Example 3, that is, EMBO CAPS VG capsule commercially marketed by Suheung Co., Ltd.

FIG. 6 is a graph showing the changes of plasma concentrations of acetaminophen according to the lapse of time, when the acetaminophen is filled and administered to the Beagles in both hypromellose hard capsule using thermogelation of the present invention and the hard capsule prepared in Comparative Preparation Example 3, that is, EMBO CAPS VG capsule commercially marketed by Suheung Co., Ltd.

As shown in the figure, the bioavailability of ingredient drug according to the hypromellose hard capsule using thermogelation of the present invention increases compared to that of cellulose capsule using a chemical gelling agent by increasing at least 5% of the AUC (Area Under Curve).

Further, such an improvement of bioavailability of hypromellose hard capsule using thermogelation by hot dipping method of the present invention has been believed that in vivo absorption, distribution and metabolism of drug ingredient have been favorably affected by proper in vivo dissolution and disintegration performance, because the hypromellose hard capsule using thermogelation does not contain any gelling agent and/or auxiliary gelling agent.

The process for preparing a hypromellose hard capsule using thermogelation of the present invention can be explained with following 3 steps.

(Step 1) Preparation of Hypromellose Aqueous Dispersion

In the first step, 0.1-0.5 wt part of propylene glycol as plasticizer, 0.1-0.5 wt part of D-sorbitol as wetting agent and 0.04-0.25 wt part of colloidal silica as viscosity stabilizer have been sequentially added and solubilized into the 100 wt part of hypromellose aqueous dispersion containing 19-22 wt part of hypromellose substitution type 2906 (0.3 wt % of NaCl content). The hypromellose aqueous dispersion has been obtained after stirring and dispersing over 3000 rpm for 4 hours.

(Step 2) Preparation of Hypromellose Aqueous Solution

In this step, the hypromellose aqueous solution has been prepared, after completely solubilizing the hypromellose aqueous dispersion obtained in Step 1 by stirring and cooling it at 30 rpm for 44-52 hours in the hydration tank maintained at 17-23° C. After measuring the initial viscosity of completely solubilized hypromellose aqueous solution, purified water has been added to adjust the final viscosity of hypromellose aqueous solution to be 800-1,300 cP. Finally, hypromellose aqueous solution has been prepared after aging for 56 hours with removal of air bubbles.

(Step 3) Preparation of Hypromellose Hard Capsule Using Thermogelation

In this step, after preheating the mold pin to be 100-120° C. by the deck heater of pinbar heating part and the pinbar pressing device, the preheated mold pin has been dipped into the hypromellose aqueous solution. Further, the temperature of the dipping pan is maintained at 19-21° C. under the control of temperature control device of dipping pan. Finally, a hypromellose hard capsule has been prepared after forming and drying it at 50-70° C., 20-85% of relative humidity for 40-80 minutes.

Therefore, a hypromellose hard capsule using thermogelation with improved storage stability, film strength, film distribution, filling up performance and/or bioavailability of ingredient can be prepared after completing said 3 steps.

The present invention can be explained more concretely by following Preparation Examples, Comparative Preparation Examples and Examples. However, it should be understood that the Examples are intended to illustrate but not in any manner to limit the scope of the present invention.

(Preparation Example) Preparation of Hypromellose Hard Capsule Using Thermogelation of the Present Invention (Step 1) Preparation of Hypromellose Aqueous Dispersion 210 g of propylene glycol as plasticizer, 210 g of D-sorbitol as wetting agent and 84 g of colloidal silica as viscosity stabilizer have been sequentially added and solubilized into the 100 Kg of hypromellose aqueous dispersion having 79 L of purified water containing 21 Kg of hypromellose substitution type 2906 (0.3 wt % of NaCl content) at 90° C. The hypromellose aqueous dispersion has been obtained after stirring and dispersing over 3000 rpm for 4 hours.

(Step 2) Preparation of Hypromellose Aqueous Solution

The hypromellose aqueous solution has been prepared, after completely solubilizing the hypromellose aqueous dispersion obtained in Step 1 by stirring and cooling it at 30 rpm for 48 hours in the hydration tank maintained at 17-23° C. After measuring the initial viscosity of completely solubilized hypromellose aqueous solution, purified water has been added to adjust the final viscosity of hypromellose aqueous solution to be 800-1,300 cP. Finally, hypromellose aqueous solution has been prepared after aging for 56 hours with removal of air bubbles.

(Step 3) Preparation of Hypromellose Hard Capsule Using Thermogelation

After preheating the mold pin to be 100-120° C. by the deck heater of pinbar heating part and the pinbar pressing device, the preheated mold pin has been dipped into the hypromellose aqueous solution. Further, the temperature of the dipping pan is maintained at 19-21° C. under the control of temperature control device of dipping pan. Then, the molded film has passed through both the tunnel heater as auxiliary gelling apparatus and drying kiln for 60 minutes. The moisturized air conditions supplied to drying kiln has been 50° C. of temperature, 50% of relative humidity (RH), 0.04 kg/kg of absolute humidity. Finally, a transparent hypromellose hard capsule size #0 with improved storage stability, film strength, film distribution, filling up performance and/or bioavailability of ingredient has been prepared.

(Comparative Preparation Example 1) Preparation of Hypromellose Hard Capsule Using Thermogelation (Excess NaCl Content in the Raw Material of Hypromellose, without Wetting Agent)

(Step 1) Preparation of Hypromellose Aqueous Dispersion 210 g of propylene glycol as plasticizer and 84 g of colloidal silica as viscosity stabilizer have been sequentially added and solubilized into the 100 Kg of hypromellose aqueous dispersion having 79 L of purified water containing 21 Kg of hypromellose substitution type 2906 (0.4 wt % of NaCl content) at 90° C. The hypromellose aqueous dispersion has been obtained after stirring and dispersing over 3000 rpm for 4 hours.

(Step 2) Preparation of Hypromellose Aqueous Solution

The hypromellose aqueous solution has been prepared, after completely solubilizing the hypromellose aqueous dispersion obtained in Step 1 by stirring and cooling it at 30 rpm for 48 hours in the hydration tank maintained at 17-23° C. After measuring the initial viscosity of completely solubilized hypromellose aqueous solution, purified water has been added to adjust the final viscosity of hypromellose aqueous solution to be 800-1,300 cP. Finally, hypromellose aqueous solution has been prepared after aging for 56 hours with removal of air bubbles.

(Step 3) Preparation of Hypromellose Hard Capsule Using Thermogelation

After preheating the mold pin to be 100-120° C. by the deck heater of pinbar heating part and the pinbar pressing device, the preheated mold pin has been dipped into the hypromellose aqueous solution. Further, the temperature of the dipping pan is maintained at 19-21° C. under the control of temperature control device of dipping pan. Then, the molded film has passed through both the tunnel heater as auxiliary gelling apparatus and drying kiln for 60 minutes. The moisturized air conditions supplied to drying kiln has been 50° C. of temperature, 50% of relative humidity (RH), 0.04 kg/kg of absolute humidity. Finally, a transparent hypromellose hard capsule size #0 has been prepared.

Finally, plating phenomenon has occurred in the obtained hypromellose hard capsule size #0. Therefore, the transparency of hypromellose hard capsule becomes declined according to the lapse of time.

(Comparative Preparation Example 2) Preparation of Hypromellose Hard Capsule Using Thermogelation (without Equipment of Pinbar Pressing Device and Temperature Control Device of Dipping Pan)

(Step 1) Preparation of Hypromellose Aqueous Dispersion 210 g of propylene glycol as plasticizer, 210 g of D-sorbitol as wetting agent and 84 g of colloidal silica as viscosity stabilizer have been sequentially added and solubilized into the 100 Kg of hypromellose aqueous dispersion having 79 L of purified water containing 21 Kg of hypromellose substitution type 2906 (0.3 wt % of NaCl content) at 90° C. The hypromellose aqueous dispersion has been obtained after stirring and dispersing over 3000 rpm for 4 hours.

(Step 2) Preparation of Hypromellose Aqueous Solution

The hypromellose aqueous solution has been prepared, after completely solubilizing the hypromellose aqueous dispersion obtained in Step 1 by stirring and cooling it at 30 rpm for 48 hours in the hydration tank maintained at 17-23° C. After measuring the initial viscosity of completely solubilized hypromellose aqueous solution, purified water has been added to adjust the final viscosity of hypromellose aqueous solution to be 800-1,300 cP. Finally, hypromellose aqueous solution has been prepared after aging for 56 hours with removal of air bubbles.

(Step 3) Preparation of Hypromellose Hard Capsule Using Thermogelation (Unstable Temperature of Pinbar and Dipping Pan)

After preheating the mold pin less than 100-120° C. by the deck heater of pinbar heating part, the preheated mold pin has been dipped into the hypromellose aqueous solution in the dipping pan maintained over 19-21° C. Therefore, the temperature of pinbar and dipping pan is unstable, because pinbar pressing device and temperature control device of dipping pan have not been equipped.

Then, the molded film has passed through both the tunnel heater as auxiliary gelling apparatus and drying kiln for 60 minutes. The moisturized air conditions supplied to drying kiln has been 50° C. of temperature, 50% of relative humidity (RH), 0.04 kg/kg of absolute humidity.

Finally, a hypromellose hard capsule size #0 cannot be prepared as a desirable shape even though the temperature of drying kiln increases over 50° C., because the obtained hypromellose hard capsule cannot have the sufficient film strength and film distribution.

Therefore, a hypromellose hard capsule using thermogelation cannot be obtained according to the preparation method in Comparative Preparation Example 2.

(Comparative Preparation Example 3) Preparation of Cellulose Hard Capsule Using a Chemical Gelling Agent (EMBO Capsule VG Commercially Marketed by Suheung Co., Ltd.)

0.6 Kg of amide pectin as gelling agent, 0.05 Kg of calcium gluconate as auxiliary gelling agent, 0.02 Kg of glacial acetic acid as pH neutralizer, 0.05 Kg of sucrose fatty acid ester as emulsifying agent and 0.01 Kg of glycerin as lubricant have been sequentially added and solubilized into the 100 Kg of cellulose aqueous solution including 79 L of purified water and 21 Kg of cellulose at 75° C. After cooling it until 45° C., a cellulose aqueous mixture has been prepared. Then, obtained cellulose aqueous mixture has stand still with adjusting the viscosity. The cellulose hard capsule size #0 has been prepared after molding and drying it after dipping the mold pin into the dipping pan at 60° C.

(Example 1) Film Transparency Test and Storage Stability 3 kinds of hard capsules size #0 prepared in Preparation Example, Comparative Preparation Example 1 and 3 have been stored in an accelerated stability chamber maintained at 40° C., 75% RH for 6 months, and have been used for measuring the film transparency and storage stability by lapse of time. The results are shown in Table 1. UV-visible spectrophotometer has been used for measuring instrument. The measurement has been performed by cutting the body of the capsule 1 cm in width and 1 cm in length, and the transparency of film has been measured at 420 nm by the UV-visible spectrophotometer.

TABLE 1

| | Film transparency test (n = 10) | | | |
|---|---|---|---|---|
| | | Prep. Ex. | Comp. Prep. Ex. 1 | Comp. Prep. Ex. 3 |
| Transparency (%) | Initial | 71% | 70% | 52% |
| | 1 month later | 71% | 64% | 50% |
| | 2 months later | 71% | 60% | 50% |
| | 3 months later | 70% | 57% | 48% |
| | 6 months later | 69% | 52% | 46% |

In the case of the hypromellose hard capsule using thermogelation prepared in Preparation Example of the present invention, the initial and 6 months later transparency have been measured to be 71% and 69% respectively, showing no significant change even after 6 months. Therefore, it has been evaluated that transparency of film and storage stability are excellent.

In the case of the hypromellose hard capsule using thermogelation prepared in Comparative Preparation Example 1 using the raw material of hypromellose having 0.4 wt % of excessive NaCl content, the initial transparency (70%) has been measured as similar to that of hypromellose hard capsule of the present invention. However, the transparency has been gradually declined according to lapse of time. After the lapse of 6 months, the transparency has been measured as 52%, which is about 17% lower compared to that of hypromellose hard capsule using thermogelation of the present invention. It has been believed that the decline of transparency of film and storage stability have been caused by the excessive 0.4 wt % NaCl content in the raw material of hypromellose and the absence of wetting agent.

On the other hand, in the case of the cellulose hard capsule using gelling agent and auxiliary gelling agent prepared by conventional cold dipping method in Comparative Preparation Example 3, it has been shown as the lowest transparency of capsule even in 52% of initial transparency.

(Example 2) Film Distribution Test 3 kinds of hard capsules size #0 prepared in Preparation Example, Comparative Preparation Example 1 and 3 have been used for measuring film distribution. As a control group, gelatin capsule #0 has been used. For measuring the film distribution, the film thicknesses of the cutting edge part and the dome part have been measured using each 100 sample capsules. The results are shown in Table 2.

TABLE 2

| | | | | | | | | (mm) |
|---|---|---|---|---|---|---|---|---|
| | Prep. Ex. | | Com. Pre. Ex. 1 | | Com. Pre. Ex. 3 | | Control | |
| | Cap | Body | Cap | Body | Cap | Body | Cap | Body |
| Cutting edge | 0.105 | 0.096 | 0.092 | 0.085 | 0.100 | 0.090 | 0.105 | 0.100 |
| Dome | 0.116 | 0.106 | 0.097 | 0.089 | 0.109 | 0.103 | 0.120 | 0.110 |

The film distribution of hypromellose hard capsule using thermogelation prepared in Preparation Example of the present invention has been improved by increasing the thickness of cutting edge and dome compared to those of prepared in Comparative Preparation Examples 1 and 3. Further, the film distribution of hypromellose hard capsule using thermogelation of the present invention has been improved as equivalent to that of conventional gelatin capsule as control group.

(Example 3) Film Strength Test 3 kinds of hard capsules size #0 prepared in Preparation Example, Comparative Preparation Example 1 and 3 have been used for measuring film strength. Texture Analyzer (Model TA 1000) has been used for measuring instrument. The descending speed of probe has been 0.5 mm/sec and the probe has been drop down 4 mm under the surface of capsule. After the hard capsules size #0 have been horizontally laid in the Texture Analyzer, the film strength has been measured from the capsule contact moment to the 4 mm below upon dropping down the probe. The results are shown in Table 3.

TABLE 3

| | | Prep. Ex. | Com. Pre. Ex. 1 | Com. Pre. Ex. 3 |
|---|---|---|---|---|
| Mechanical film strength (g) | Maximum | 460 | 285 | 300 |
| | Average | 370 | 230 | 265 |
| | Minimum | 310 | 180 | 220 |

The film strength of hypromellose hard capsule using thermogelation prepared in Preparation Example of the present invention has been shown as 370 g, while the film strengths of hard capsules prepared in Comparative Preparation Example 1 and Comparative Preparation Example 3 have been shown as 230 g and 265 g respectively. Therefore, hypromellose hard capsule using thermogelation of the present invention has shown the better mechanical film strength.

(Example 4) Dissolution Test 2 kinds of hard capsules size #0 prepared in Preparation Example and Comparative Preparation Example 3 have been used for testing dissolution profile after filling acetaminophen. The dissolution profiles of acetaminophen have been measured in Test fluid 1 (pH 1.2), Test fluid 2 (pH 6.8) and purified water (pH 7.0) for 60 minutes according to the paddle method of dissolution test in Korean pharmacopoeia 10th Edition.

Table 4 shows the results of dissolution rate (%) of acetaminophen in Test fluid 1 (pH 1.2). Test fluid 1 has been prepared by adding and stirring 250 ml of KCl solution, 425 ml of 0.2 M HCl solution and purified water to be 1,000 ml of test fluid.

TABLE 4

| | Time (minutes) | | | | |
|---|---|---|---|---|---|
| | 0 | 15 | 30 | 45 | 60 |
| Prep. Ex. | 0 | 80.2 | 96.4 | 97.8 | 98.5 |
| Comp. Prep. Ex. 3 | 0 | 70.7 | 90.5 | 93.3 | 97.2 |

Table 5 shows the results of dissolution rate (%) of acetaminophen in Test fluid 2 (pH 6.8). Test fluid 2 has been prepared by adding and stirring 250 ml of $KH_2PO_4$ solution, 112 ml of NaOH solution and purified water to be 1,000 ml of test fluid.

TABLE 5

| | Time (minutes) | | | | |
|---|---|---|---|---|---|
| | 0 | 15 | 30 | 45 | 60 |
| Prep. Ex. | 0 | 78.8 | 96.1 | 98.1 | 98.6 |
| Comp. Prep. Ex. 3 | 0 | 73.7 | 94.6 | 96.3 | 97.9 |

Table 6 shows the results of dissolution rate (%) of acetaminophen in purified water (pH 7.0).

TABLE 6

| | Time (minutes) | | | | |
|---|---|---|---|---|---|
| | 0 | 15 | 30 | 45 | 60 |
| Prep. Ex. | 0 | 82.2 | 95.4 | 97.2 | 98.9 |
| Comp. Prep. Ex. 3 | 0 | 79.4 | 93.5 | 96.3 | 98.2 |

Hypromellose hard capsule using thermogelation prepared in Preparation Example of the present invention has shown the better dissolution rate compared to that of cellulose hard capsule using a chemical gelling agent, EMBO Capsule VG commercially marketed by Suheung Co., Ltd. In detail, the dissolution rate in Test fluid 1 (pH 1.2) of Hypromellose hard capsule of the present invention shows better dissolution rate compared to that of cellulose capsule, at least 10% better dissolution at 15 minutes. However, the dissolution rate in Test fluid 2 (pH 6.8) and purified water (pH 7.0) cannot show the significant differences of dissolution rate compared to those of cellulose capsule.

(Example 5) Filling Up Performance Test

Hypromellose hard capsule using thermogelation prepared in Preparation Example of the present invention and cellulose hard capsule prepared in Comparative Preparation Example 3, EMBO Capsule VG commercially marketed by Suheung Co., Ltd. have been used for filling up performance test. The results are shown in Table 7.

TABLE 7

| Machine type | | EXC-100F (Suheung Co., Ltd.) | | |
|---|---|---|---|---|
| Speed | | 50,000 ea/hr | | 100,000 ea/hr |
| Vacuum pressure | | 20 cmHg | | 20 cmHg |
| Quantity | | 500,000 ea | | 500,000 ea |
| | | Prep. Ex. | Com. Pre. Ex. 3 | Prep. Ex. | Com. Pre. Ex. 3 |
| defect | telescope | 1 | 8 | 1 | 10 |
| | dent | 0 | 4 | 0 | 5 |

As shown in Table 7, hypromellose hard capsule using thermogelation prepared in Preparation Example of the present invention has shown the better filling up performance compared to that of cellulose hard capsule using a chemical gelling agent prepared in Comparative Preparation Example 3 according to the improvement of film strength of the capsule. It has been confirmed that the defects including telescope and dent have significantly decreased in hypromellose hard capsule of the present invention.

(Example 6) Bioavailability Test

Hypromellose hard capsule using thermogelation prepared in Preparation Example of the present invention and cellulose hard capsule prepared in Comparative Preparation Example 3, EMBO Capsule VG commercially marketed by Suheung Co., Ltd. have been used for bioavailability test after filling acetaminophen. The bioavailability test has been measured by the plasma concentration of acetaminophen in test animal of Beagles according to lapse of time.

6 animals have been divided into 2 groups and each group has 3 test animals. Each 250 mg of acetaminophen has been filled into the hard capsules prepared in Preparation Example and Comparative Preparation Example 3, and hard capsules have been orally administered to the test animals of Beagles. For evaluating the bioavailability, the plasma concentrations of acetaminophen in test animals have been measured by every hour for 8 hours. The pharmacokinetic parameters have been analyzed. The results are shown in FIG. 6 and Table 8.

FIG. 6 is a graph showing the changes of plasma concentrations of acetaminophen according to the lapse of time, when the acetaminophen is filled and administered to the Beagles in both hypromellose hard capsule using thermogelation of the present invention and the hard capsule prepared in Comparative Preparation Example 3, that is, EMBO CAPS VG capsule commercially marketed by Suheung Co., Ltd.

TABLE 8

| Pharmacokinetic parameters | | |
|---|---|---|
| | Prep. Ex. | Com. Pre. Ex. 3 |
| AUC (µg · hr/ml) | 142.3 | 134.8 |
| $C_{max}$ (µg/ml) | 76.1 | 81.0 |
| $T_{max}$ (hour) | 0.95 | 0.98 |

Hypromellose hard capsule using thermogelation prepared in Preparation Example of the present invention has shown the better bioavailability compared to that of cellulose hard capsule prepared in Comparative Preparation Example 3, EMBO Capsule VG commercially marketed by Suheung Co., Ltd.

In detail, the value of the maximum plasma concentration ($C_{max}$) of cellulose hard capsule prepared in Comparative Preparation Example 3, EMBO Capsule VG is slightly higher than that of hypromellose hard capsule using thermogelation of the present invention. Even though the time required for maximum plasma concentration ($T_{max}$) cannot have a significant difference, in terms of the bioavailability evaluating value of AUC (Area Under Curve), the AUC value of hypromellose hard capsule using thermogelation prepared in Preparation Example of the present invention increases at least 5.0% compared to that of cellulose hard capsule prepared in Comparative Preparation Example 3, EMBO Capsule VG commercially marketed by Suheung Co., Ltd.

Therefore, it has been confirmed that hypromellose hard capsule using thermogelation of the present invention shows the better bioavailability of ingredient, by at least 5% increase of AUC value compared to that of commercially available cellulose capsule using a chemical gelling agent.

What is claimed is:

1. A process for preparing a hypromellose hard capsule using thermogelation with storage stability, film strength, film distribution, filling up performance and/or bioavailability of ingredient comprising the steps of:
    i) sequentially adding and solubilizing 0.1-0.5 wt part of propylene glycol as plasticizer, 0.1-0.5 wt part of D-sorbitol as wetting agent and 0.04-0.25 wt part of colloidal silica as viscosity stabilizer into the 100 wt part of hypromellose aqueous dispersion containing 19-22 wt part of hypromellose, and dispersing them 4 hours, wherein the amount of sodium chloride in raw material of hypromellose is less than 0.3 wt %;
    ii) completely solubilizing the hypromellose aqueous dispersion obtained in step i) to be transparent liquid phase by standing still for 44-52 hours at 17-23° C. in a hydration tank;
    iii) adjusting the final viscosity of hypromellose aqueous solution into 800-1,300 cP;
    iv) dipping a preheated mold pin into the hypromellose aqueous solution in the dipping pan maintained at 19-21° C. under the control of temperature control device of dipping pan after preheating the mold pin to be 100-120° C. in a deck heater of pinbar heating part; and
    v) forming and drying the obtained hard capsule at 50-70° C., 20-85% of relative humidity for 40-80 minutes.

2. The process for preparing a hypromellose hard capsule using thermogelation according to claim 1, wherein said deck heater in the pinbar heating part is installed for heating the mold pin to maintain the uniform film thickness in the range of 0.08-0.12 mm, and said deck heater is constructed by stacking a ceramic sliding plate and an aluminum heating plate on a mica plate heater on a urethane insulation base.

3. The process for preparing a hypromellose hard capsule using thermogelation according to claim 2, wherein a pinbar pressing device is installed for minimizing the bending of pinbar occurred when the mold pin is preheated by deck heater of pinbar heating part, and the pressing pad in the pinbar pressing device is down for pressing the upper part of mold pinbar by the pressure of compression spring.

4. The process for preparing a hypromellose hard capsule using thermogelation according to claim 1, wherein said temperature control device of dipping pan is installed for maintaining the temperature of hypromellose aqueous solution in the dipping pan to be 19-21° C. stably, by controlling the supply and return of chilled water, and the hypromellose aqueous solution is stirred at 20-28 rpm in the dipping pan.

5. The process for preparing a hypromellose hard capsule using thermogelation according to claim 1, wherein said D-sorbitol as wetting agent is added by preventing the Plating of capsule in the step iv) caused by elution of NaCl out of the hypromellose aqueous solution.

* * * * *